United States Patent [19]
Cocozza

[11] Patent Number: 5,033,463
[45] Date of Patent: Jul. 23, 1991

[54] MULTI-DOSE INHALER FOR MEDICAMENTS IN POWDER FORM

[75] Inventor: Salvatore Cocozza, Milan, Italy

[73] Assignee: Miat S.p.A., Milan, Italy

[21] Appl. No.: 601,417

[22] Filed: Oct. 22, 1990

[30] Foreign Application Priority Data

Oct. 27, 1989 [IT] Italy .................. 22172 A/89

[51] Int. Cl.[5] .......................................... A61M 15/00
[52] U.S. Cl. ......................... 128/203.21; 128/203.23
[58] Field of Search ............... 128/203.19, 203.21, 128/203.23, 203.12, 200.24, 200.23

[56] References Cited

U.S. PATENT DOCUMENTS

| | | | |
|---|---|---|---|
| 3,027,897 | 4/1962 | Carofiglio | 28/203.23 X |
| 3,906,950 | 9/1975 | Cocozza | 128/203.21 X |
| 3,971,377 | 7/1976 | Damani | 128/203.21 X |
| 4,105,027 | 8/1978 | Lundquist | 128/203.21 X |
| 4,116,195 | 9/1978 | James | 128/203.21 X |
| 4,524,769 | 6/1985 | Wetterlin | 128/203.12 X |
| 4,739,754 | 4/1988 | Shaner | 128/203.23 X |
| 4,884,565 | 12/1989 | Cocozza | 128/203.27 |

FOREIGN PATENT DOCUMENTS 2926659 1/1981 Fed. Rep. of Germany ............ 128/203.12

Primary Examiner—Edgar S. Burr
Assistant Examiner—E. P. Raciti
Attorney, Agent, or Firm—Ladas & Parry

[57] ABSTRACT

A multi-dose inhaler (1; 2) for medicaments in powder form comprises a container unit (24; 124) for the medicament in powder form, a withdrawal and dose preparation unit (22, 26; 122, 126) for the medicament, and a unit (16, 50; 152, 176) for mixing the dose of medicament with an air stream. The withdrawal and dose preparation unit comprises: a cup-type conveyor device (22; 122) provided with at least one cup (20; 120) for withdrawing from the container unit a certain quantity of powder and conveying it into a dispensing position, the cup (20; 120) having two coaxial identical holes (56; 156); and a plunger-type dispensing device (36; 106) disposed above the mixing unit, the plunger (36; 106) being insertable as an exact fit into and withdrawable from the holes (56; 156) in the cup (20; 120) when the latter is in the dispensing position, to cause a dose of medicament in powder form to fall into the mixing unit.

13 Claims, 4 Drawing Sheets

MULTI-DOSE INHALER FOR MEDICAMENTS IN POWDER FORM

BACKGROUND OF THE INVENTION

1. Field of the Invention

This invention relates to inhalers for bronchial or nasal administration of a dose of medicament in fine or micronized powder form.

2. Description of the Prior Art

Inhalers of this type are well known and can be divided substantially into two categories.

A first category comprises inhalers which use capsules normally formed of rigid gelatin or or another atoxic material. Each capsule contains a fixed quantity of powdered medicament forming the dose to be inhaled. Such inhalers comprise device for perforating or more generally opening (by various means) the capsule which is inserted into the inhaler when required.

An air stream generated by a sucking action by the user removes the contained powder from the opened capsule. The empty capsule is then expelled from the inhaler, which is then ready to receive the next capsule. In a known type of inhaler (see U.S. Pat. No. 3,906,950 and U.S. Pat. No. 4,013,075) the capsule when perforated at both its ends is held still during inhalation. The air stream which passes through it as a result of the inhalation removes the powdered medicament from its interior.

In another type of inhaler (see U.S. Pat. No. 3,807,400 and U.S. Pat. No. 3,991,761) the capsule, previously opened by suitable means, is set into movement by the action of the air stream produced by the inhalation, and is completely emptied thereby.

A further type of known inhaler (see EP-A-0 211 595) does not use individual capsules but instead is loaded with a disc-shaped pack comprising close to its periphery a series of blisters equidistant from each other and from the centre of the pack. These blisters contain a fixed quantity of powdered medicament. This pack is placed on a circular tray forming part of the inhaler and rotatable about its central axis. The tray contains holes in positions corresponding with the individual blisters and allows each blister to be moved into a predetermined position in which the blister is broken by a suitable opening device, so releasing the powder, which can then be inhaled.

Another type of inhaler, known as a multi-dose inhaler because it comprises a container containing a quantity of medicament sufficient for several doses, is described in EP-A-0 069 715 and in addition to the container comprises a device for withdrawing the powdered medicament contained in the container and for preparing the dose. This withdrawal and dose preparation device comprises a plate having a certain thickness and comprising a certain number of through holes. The plate can be moved from a position in which by mechanical means a proportion of the holes are filled with powdered medicament taken from the container, to another position in which the holes filled with medicament are located within a channel. Air flows into this channel as a result of suction provided by the user via a suction mouth in communication with the channel, to remove the powdered medicament from said holes. A scraper device is also provided to level the powder in the plate holes on that side facing the container. According to the inventor this scraper should ensure complete filling of said holes and consequently a constant dose. Although in the EP 715 document this scraper is stated to be optional, it must be considered essential for the proper operation of the inhaler because in its absence an extremely variable dose is obtained. This is because it is extremely easy for the respective holes not to be completely filled with powdered medicament because of the poor flowability of the powders used.

However even with the scraper present, the holes in the plate are not always completely filled, and there is thus an excessive dosage variability which, especially in the case of medicaments to be dispensed in very small doses, could result in substantial inactivity of the medicament.

Such multi-dose inhaler can also comprise rotary means (a rotatable impeller in the embodiment illustrated in EP-A-0 069 715) the purpose of which is to disintegrate any agglomerations of medicament particles.

Compared with inhalers using capsules containing a fixed quantity of medicament, multi-dose inhalers have undoubted advantages of convenience and marketability. However such inhalers suffer from substantial drawbacks particularly connected with the dose preparation device which, as already stated, is intrinsically unsuitable for dispensing sufficiently precise and constant amounts. The result is that powder quantities (doses) and hence medicament quantities are dispensed which do not conform to the declared quantity and are not constant. In addition the dispensed quantity is difficult to check by the appropriate authority.

Other drawbacks of known multi-dose inhalers are as follows:

although being single-piece devices, the powdered medicament contained in them is insufficiently protected, even if packaged in containers together with moisture absorption means;

the powder drawn in is insufficiently mixed with the air (ie the resultant mixture contains an insufficient air quantity for the powder quantity drawn in at each inhalation);

the air connections are always of small size, making them difficult to draw through by the user.

SUMMARY OF THE INVENTION

The main object of the present invention is to provide an inhaler of multi-dose type (i.e., provided with a container containing a powdered medicament quantity sufficient for several doses) comprising a withdrawal and dose preparation device for the powdered medicament which ensures sufficiently precise and constant dose preparation, even for small doses.

A further object of the invention is to obviate the other aforementioned drawbacks of known multi-dose inhalers.

The aforementioned main object is attained according to the present invention by a multi-dose inhaler comprising a container unit for the medicament in powder form, a withdrawal and dose preparation unit for the medicament, and a unit for mixing the dose of medicament with an air stream which is generated within a duct as a result of inhalation by the user. The withdrawal and dose preparation unit comprises: a cup-type conveyor device provided with at least one cup for withdrawing from the container unit a certain quantity of powder and conveying it into a dispensing position, the cup having two coaxially arranged identical holes; and a plunger-type dispensing device disposed above the mixing unit. The plunger is insertable as an exact fit into and withdrawable from said cup holes when the cup is in the dispensing position, to cause a dose of medicament in powder form to fall into the mixing unit.

According to one embodiment of the present invention, a wall separates the withdrawal and dose preparation unit from the mixing unit, an aperture being automatically openable in the wall to enable the dose of medicament in powder form to fall into the mixing unit following operation of the plunger when the conveyor device is in the dispensing position.

Conveniently, the multi-dose inhaler is provided with means for producing vibrations. The effect produced by these vibration-producing means facilitates the flow of the powder from the container unit to the mixing unit, and the complete filling of the cup or cups of the conveyor device.

The vibration-producing means can be operated either directly by the movement of the conveyor device or independently of it. The conveyor device can be operated by a suitable manual operating means, such as a simple knob, which transmits movement to the conveyor device by means of a shaft. Alternatively, the conveyor device can be motorized. For this purpose an electric stepping micro-motor can be used, preferably powered by batteries contained within the body of the inhaler. These batteries can also be of the rechargeable type.

If the vibration-producing means are independent of the conveyor device, they can be operated either manually or by a suitable micro-motor.

The dispensing piston device is preferably manually operated by its own operating means, such as a simple button to press with the fingers. There is however nothing to prevent the dispensing device being operated by a micro-motor, powered by the aforementioned batteries.

An elastic return means, such as a simple spring, returns the plunger to its initial position. If all or some of the devices of the inhaler are motorized, it can be convenient to provide a microprocessor means which controls all of the motorized devices in accordance with a predetermined program.

The inhaler can be of the disposable type so as to be thrown away when the powder is finished. Alternatively it can be of the rechargeable type, in which case it can comprise a container unit of replaceable type, so that when empty of powder it can be replaced with a new container unit full of powder. Again, the container can be of openable type and be refilled with the scheduled quantity of powder, provided for example in sealed sachets.

The inhaler can also be provided with a conventional device for indicating when the container is empty of powder. For example when the last useful dose has been dispensed, a warning light or other suitable signal appears.

Preferably, the signal appears when a predetermined number of doses are still available before the medicament has been totally consumed. In this manner the user has sufficient time to acquire a new inhaler or recharge it before being completely depleted of doses.

In one embodiment of the invention, to enable the door provided in the wall separating the withdrawal and dose preparation unit from the mixing unit to be automatically opened in a very simple manner, the plunger of the dispensing device comprises a coaxial needle fixed to the front face of the plunger. When the plunger is operated, this needle automatically opens the door. The needle has a sufficiently small cross-section to prevent any significant compression of the powder contained in the cup before the needle opens the door. Any compression of the powder could cause its compaction, with all the obvious drawbacks associated therewith.

When the plunger returns to its rest position a return spring automatically closes the door.

According to a further embodiment of the invention, instead of the rotatable door and needle combination, a device can be provided comprising a mobile plate or the like which moves perpendicularly to the direction of movement of the plunger and is automatically operated as a result of the operation of the latter, to cause the dose of medicament in powder form to fall into the underlying mixture unit. In particular, the mobile plate can comprise a hole of the same size as the coaxial holes in the cup of the conveyor device, such plate being mobile between two positions, namely a rest position in which the mobile plate closes the communication between the cup and the mixing unit, and a second position in which the hole in said mobile plate coincides coaxially with said two holes in the cup.

If the particular powdered medicament used should undergo compaction by the action of said needle, instead of the needle-type opening device a common opening device comprising levers operated by the movement of the plunger could be conveniently used.

The unit for mixing the dose of medicament in powder form with an air stream generated by the sucking action of the user comprises a channel through which said air stream flows. The sucking action is normally exerted through a mouthpiece about which the user can place his lips.

If the dose of medicament in powder form is to be administered nasally, the inhaler is provided with a suitable nasal adaptor or the mouthpiece is shaped to adapt to the nostril.

Conveniently, means are provided in the mixing unit of the multi-dose inhaler according to the present invention to disintegrate any agglomerates of medicament particles which can form for various reasons. In particular, it is advisable to provide such disintegration means if the device for opening the door which closes the passage between the withdrawal and dose preparation unit and the mixing unit is of needle type.

The means for disintegrating the powdered medicament can be of rotatable type (such as a rotatable impeller) or of fixed type (such as a fixed helical element).

BRIEF DESCRIPTION

The invention will be more apparent from the following description of two embodiments thereof given by way of example. In this description reference is made to the accompanying drawings, in which.

DETAILED DESCRIPTION OF THE PREFERRED EMBODIMENTS

Figure 1:
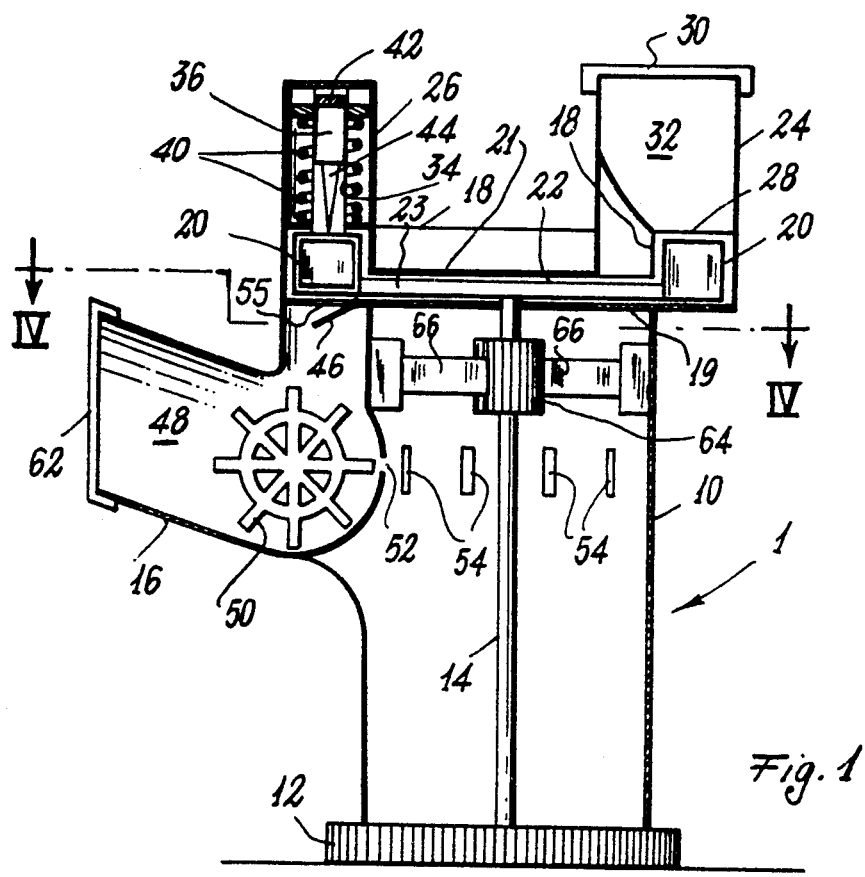
FIG. 1 is a schematic vertical sectional view of a multi-dose inhaler according to the present invention, taken on the mouthpiece axis.
Figure 2:
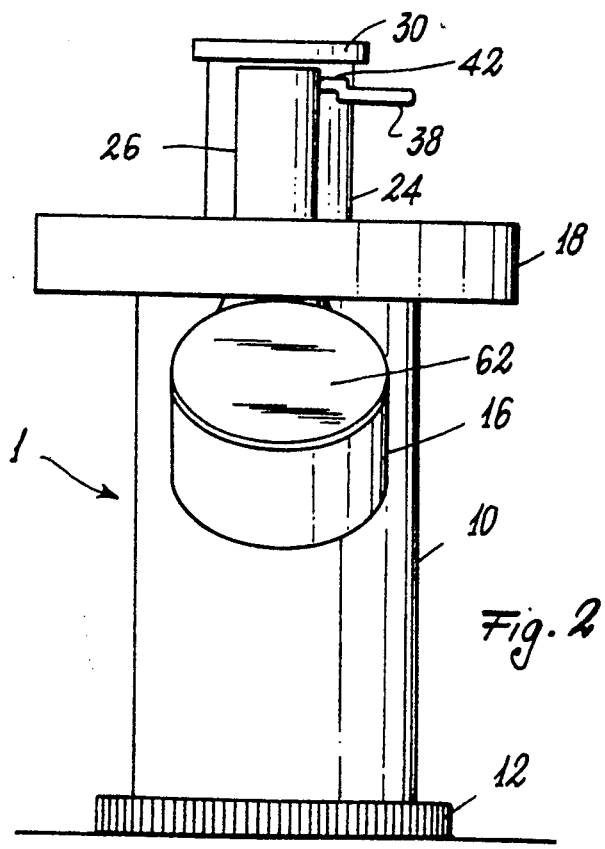
FIG. 2 is a front view thereof.
Figure 3:
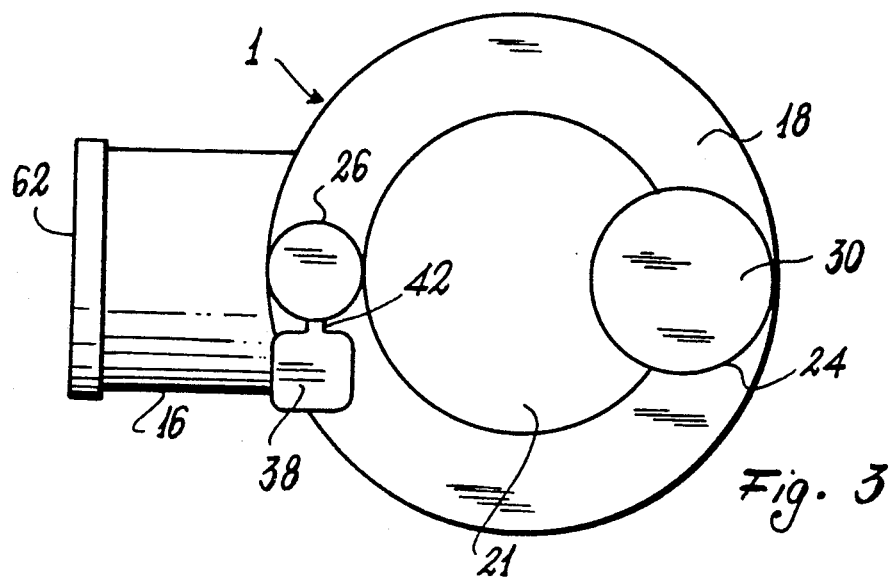
FIG. 3 is a top plan view thereof.
Figure 4:
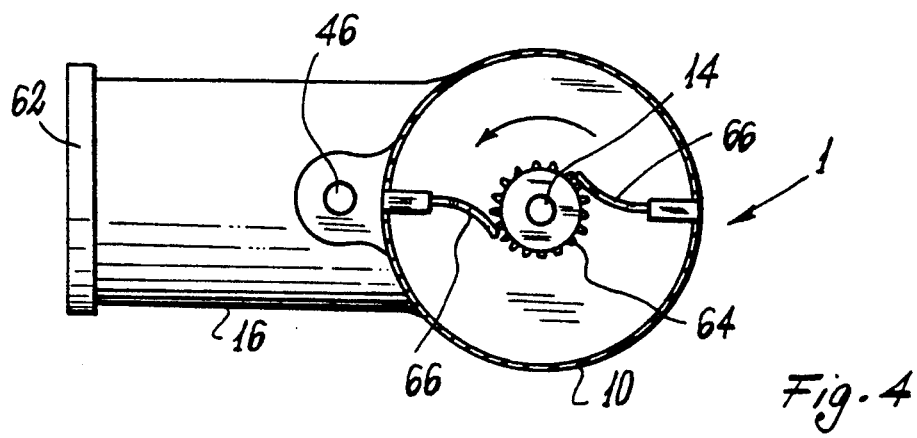
FIG. 4 is a horizontal cross-section therethrough on the line IV—IV of FIG. 1.

From FIGS. 1 to 6 it can be seen that the inhaler 1 consists substantially of a hollow cylindrical body 10 closed at its bottom by a knurled coaxial knob 12 which projects a little beyond the body 10.

A mouthpiece 16 projects laterally from the cylindrical body 10 of the multi-dose inhaler 1.

Above the cylindrical body 10 there is the withdrawal and dose preparation unit, which comprises an annular hollow enclosure or channel 18 enclosing the conveyor device 22. The cups 20, fixed to one end of a horizontal arm 23, can slide within the annular hollow enclosure 18, which is of rectangular cross-section. The other end of the arm 23 is fixed to the upper end of a vertical shaft 14 coaxial to the knurled knob 12. The arms 23 can rotate within a disc-shaped space which is peripherally in communication with the channel 18, enclosed between a lower wall 19 which closes the cylindrical body 10 near its top, and an upper wall 21 defined by the channel 18.

In the lower wall 19 there is provided a hole through which the shaft 14 passes in a sealed manner. The lower end of the shaft 14 is fixed to the center of the knob 12, so that on operating the latter the arms 23 with their relative cups 20 rotate in a horizontal plane.

A first cylindrical enclosure 24 forming the container unit for the medicament in powder form and a second cylindrical enclosure 26 enclosing the actual dispensing device project upwards from the top of the inhaler 1.

The container 24, internally in the form of a hopper 32, communicates via a base aperture 28 with the channel 18 within which the cups 20 slide. The container 24 is closed at its top by a cap 30.

The cylindrical enclosure 26 encloses a vertical cylindrical guide 34 within which the plunger 36 can slide in both directions. A lateral knob 38 (FIGS. 2 and 3) fixed to the top of the plunger 36 by a connection stem 42, allows the plunger 36 to be pushed downwardly. The stem 42 can slide in a vertical slot (not shown in the figures) which extends laterally through the entire height of the cylindrical enclosure 26. A helical return spring 40 returns the plunger 36 into its upper position shown in FIG. 1, this being its normal position (or rest position) when the knob 38 is not pressed. A coaxial needle 44 is fixed to the lower face of the plunger 36 to automatically anticipate the opening of the door 46 provided in the base of the channel 18 at the plunger 36. The door 46 is provided with a suitable return spring (not shown in the figures) which closes it automatically when the needle 44 disengages from it.

Although for clarity the needle 44 is shown in FIG. 1 with rather large transverse dimensions, in reality it will have only a minimum transverse dimension, compatible with constructional requirements and its mechanical strength. This means that the medicament in powder form contained in the cup 20 is compacted as little as possible when the needle 44 passes through it.

Although the described device for opening the door 46 is very simple, it is apparent to the expert of the art that other opening devices for this door could equally be used. As already stated, the opening can for example be controlled by suitable levers (not shown) operated by the movement of the plunger 36. This thus obviates any compression of the powdered medicament due to the presence of a needle 44, especially if the particles of medicament have the tendency to agglomerate.

As can be seen from FIG. 1, the door 46 connects the channel 18 to the mixing channel 48 within the mouthpiece 16. This mixing channel contains a conventional impeller 50 which is rotatable about its own horizontal axis and is located below the door 46.

In the vicinity of the impeller 50 there is provided a suitably sized air port 52 which connects the mixing channel 48 to the interior of the cylindrical body 10.

Suitable slots 54 provided in the side wall of the cylindrical body 10 enable external air to enter it. In the illustrated embodiment two diametrically opposing cups 20 are provided, so that the relative arms 23 are coaxial. It is however apparent that these cups can be other than two in number, or even just one. The cups 20 can have the shape shown in FIG. 5 or FIG. 6. Specifically, in FIG. 5 the cup is of parallelepiped shape and is open at its front face. The upper and lower faces of the parallelepiped comprise two coaxial circular holes 56, of such dimensions in to receive the plunger 36 as an exact fit. Conveniently the holes 56 are tangential to the inner walls of the cups 20.

Figure 5:
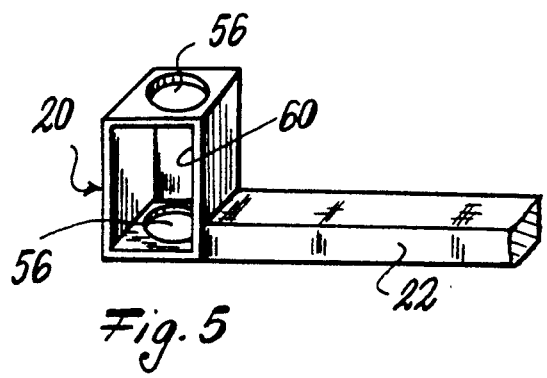
FIG. 5 is a perspective view of a cup of the conveyor device.
Figure 6:
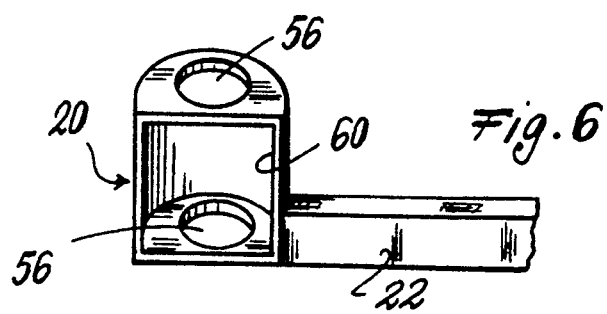
FIG. 6 is a modification of the cup of FIG. 5.
Figure 7:
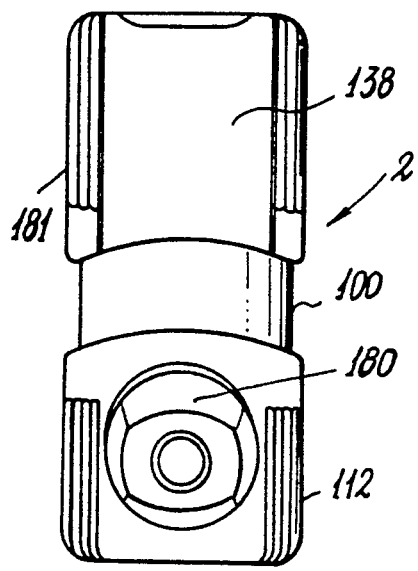
FIG. 7 is a front view of a second embodiment of an inhaler according to the invention.
Figure 8:
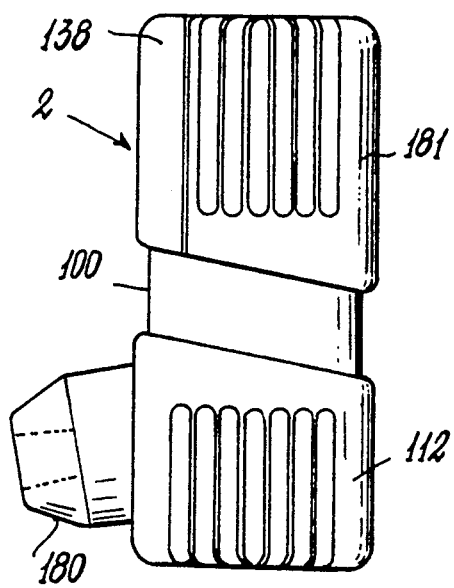
FIG. 8 is a side view thereof.
Figure 9:
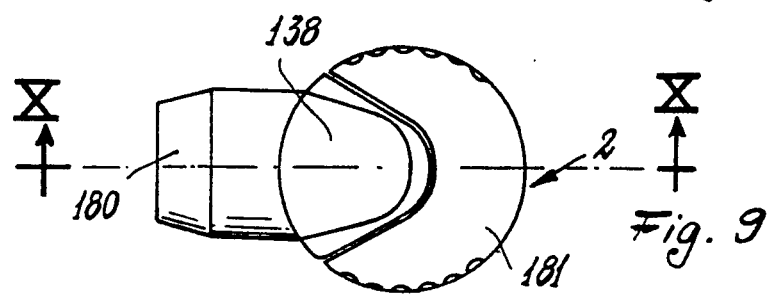
FIG. 9 is a top plan view thereof.

In FIG. 6 the cup is of semicylindrical shape, but is otherwise identical to that of FIG. 5. The holes 56 are again tangential to the semicylindrical inner wall of the cup 20. By means of suitable notches (not shown in the figures) provided on the knurled knob 12 and corresponding notches (also not shown) provided on the lower outer part of the cylindrical body 10, it is possible by rotating the knob to position one of the cups 20 such that the two opposing coaxial holes 56 in the cup 20 are coaxial with the plunger 36. Instead of said notches other conventional means for identifying said predetermined positions can be used.

As stated, to facilitate movement of the powder, the inhaler 1 is provided with means for producing vibrations. In this specific case, said means consist of a knurled drum 64 arranged coaxially on the shaft 14. The ends of two preloaded elastic blades 66 slide along the surface of the drum 64, their other ends being fixed to the interior of the cylindrical body 10. Other conventional means for producing vibrations, including motorized means, can however be usefully used.

The operation of the multi-dose inhaler 1 is apparent from the aforegoing description. However a short description is given hereinafter for greater clarity.

It will be assumed that the hopper 32 of the container 24 already contains a quantity of medicament in powder form sufficient for a certain number of doses, for example 100. The powder can fall by gravity (aided by the action of said vibration-production means 64, 66) through the lower aperture 28 of the hopper 32 and into the annular channel 18 within which the cups 20 move. These latter have their mouth 60 facing the direction of advancement so that in passing from the first withdrawal position (corresponding to the container 24) to the second dispensing position (corresponding to the plunger 26) the cups 28 become completely filled with powder.

When a cup 20 is in the the second position (the holes 56 being coaxial with the plunger 36), on pressing the knob 38 which operates the plunger 36, this latter is lowered. The needle 44 of the plunger 36 passes through the powder contained in the cup 20 by passing through the holes 56, to open the door 46. The subsequent action of the plunger 36, which operates in the manner of a punch, causes a certain quantity of powder to fall onto the impeller 50 in the mixing channel 48. On releasing the knob 38 the plunger 36 returns to its normal position under the action of the return spring 40, and the door 46 recloses. If the user now removes the cap 62 and sucks through the mouthpiece 16 with his mouth, he generates an air stream, which is drawn from the outside through the slots 54 and passes through the aperture or apertures 52. This air stream causes the impeller 50 to rotate at a speed so as to mix, so in the best possible manner with the air, the dose of powder which has fallen onto the impeller 50. The air stream loaded with powder then proceeds towards the mouth of the mouthpiece, to enter the oral cavity of the patient.

The cross-section of the slots 54 and the aperture or apertures 52 must be such as not to compel the user to use excessive sucking force, as happens in the case of many known multi-dose inhalers.

If inhalation is to take place through a nostril, the inhaler is provided for this purpose with a suitable adaptor to fit onto the mouthpiece 16. Alternatively, this latter can be shaped to adapt to the nostril.

The fall of the powder from the hopper 32 into the channel 18 and the complete filling of the cups 20 are facilitated by the provision of the a forementioned vibration-producing means.

The illustrated inhaler is of the manually operated type. However a stepping micro-motor and the necessary transmission and rotation reduction elements can be easily fitted into the cylindrical body 10 to transmit movement to the shaft 14 and consequently to the cup conveyor device 22.

Instead of the knurled drum 64 and blades 66 a conventional motorized vibration-producing means can be accommodated in the same free space, for example an eccentric member rotated by the aforesaid micro-motor or another micro-motor.

The movement of the plunger 36 and, in the limit, the opening of the door 46 can be motorized by a micromotor.

All these micro-motors are powered by batteries, possibly of rechargeable type, conveniently situated in the cylindrical body 10.

A conventional device (not shown in the embodiment of FIGS. 1–6) can also be provided to indicate, by lighting a warning lamp or similar means, that the last useful dose has been delivered or preferably that the medicament will have been completely consumed after a certain remaining number of doses. From tests carried out it has been found that the multi-dose inhaler according to the present invention attains the a forementioned objects. In particular it provides doses which fall within the narrow tolerances defined for dispensers of small doses of medicament in powder form.

Finally, a microprocessor can be provided to control all or part of the previously described motorized devices, in accordance with a predetermined program.

FIGS. 7 to 10 show a second multi-dose inhaler according to the present invention. As is apparent from these figures the inhaler 2 is of particularly compact form in addition to being completely manual operation and providing high precision in dispensing the medicament in powder form. The inhaler 2 is particularly suitable for plastics construction.

Figure 11:
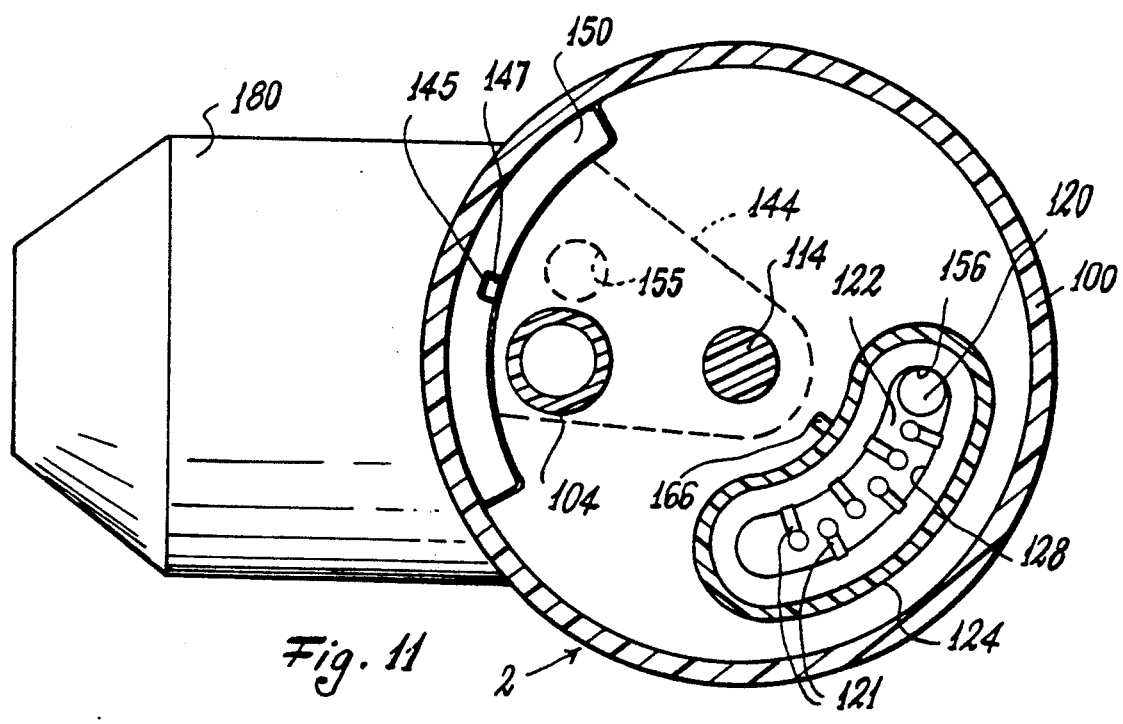
FIG. 11 is a horizontal section therethrough on the line XI—XI of FIG. 10, but with the mouthpiece closure cap removed.
Figure 10:
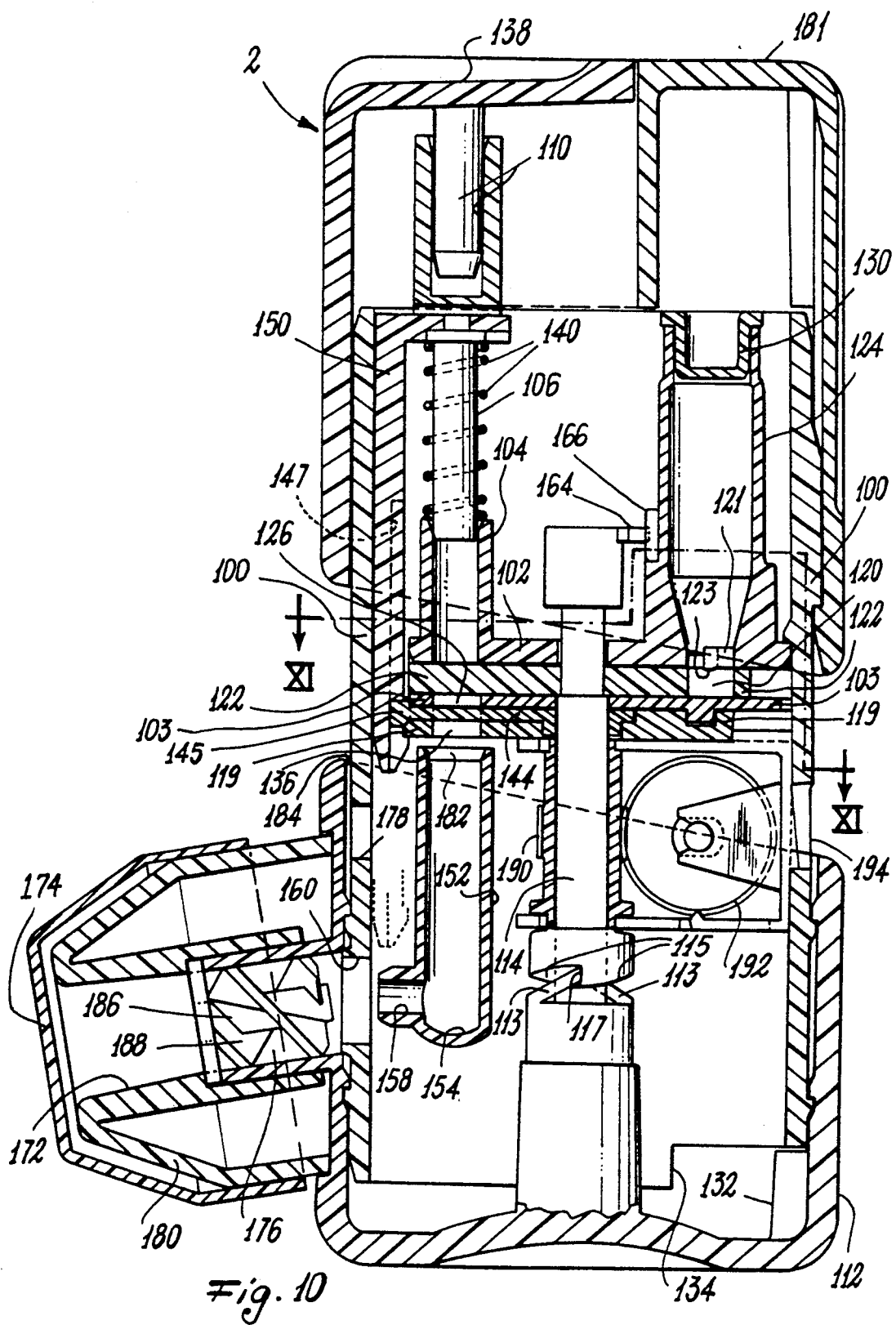
FIG. 10 is a vertical section on the line X—X, there being also provided a closure cap on the mouthpiece.

As can be seen from FIG. 10, the inhaler 2 comprises a cylindrical body 100. In the cylindrical body 100 there is provided a container 124 of hopper shape. This container, which in FIG. 10 appears to be rather small, has in effect an elongate shape when viewed in plan, as can be seen in FIG. 11.

In any event the capacity of the container 124 will be made proportional to the predetermined number of medicament doses required to be dispensed by the inhaler 2.

The container 124 comprises a circular upper aperture for loading the medicament in powder form, and closed by a stopper 130.

As can be seen from FIG. 10 the container 124 is fixed by a support element 102 which is overall of disc shape.

This latter also carries a cylindrical sleeve 104 having a vertical axis and constructed integrally with the support disc 102 and extending upwards from the upper face of the disc 102.

Sleeve 104 acts as a guide for a plunger 106 mobile vertically in both directions and forming part of the dispensing device for the powdered medicament.

When at rest, the plunger 106 is kept in its highest position (FIG. 10) by the helical return spring 140. The upper end of the plunger 106 is fixed by a male and female forced connection 110 to the knob 138, which can be pressed downwards. Consequently on pressing the knob 138 the plunger 106 is lowered.

The invention 2 is closed at its top both by the knob 138 and by a closure cap 181 snap-fitted onto the cylindrical body 100.

Below the support disc 102 and in contact therewith there is a disc-shaped conveyor 122 comprising a single cup 120. The conveyor 122 is mounted coaxially to the support disc 102 and rests on the horizontal plate 119 of the cylindrical body 100.

The disc conveyor 122 is fixed onto a vertical shaft 114 and rests on an intermediate disc 103 rotatably fixed on the plate 119 rigid with the cylindrical body 100. As stated, the disc conveyor 122 has only one cup, which consists very simply of a through hole 120 with two identical apertures 156, namely an upper and a lower. The dimensions of the cup 120 are such that it contains one dose of medicament to be dispensed.

The shaft 114 can be rotated between two predetermined angular positions by a lower rotatable knob 112. The knob 112 is connected to the shaft 114 by a free release mechanism visible in FIG. 10 and consisting in known manner of a pair of elastic tongues 113 engaging corresponding portions of a helical surface 115.

Two limit stops, of which only one (the step 117) is visible in FIG. 10, allow the knob to rotate through an angle of approximately 180° between two positions, namely a position, known hereinafter as the filling commencement position, in which the cup 120 of the conveyor disc 122 is in the situation illustrated in FIG. 11 (i.e., at one end of the base slot 128 in the container 124), and a position which has already been defined heretofore as the dispensing position in which the cup 120 of the conveyor disc 122 coincides with the hole 126 in the intermediate disc 103, the hole 126 being coaxial with a hole 136 provided in the plate 119.

When the cup 120 is in the dispensing position, the lug 132 of the knob 112 is against the step 134 on the cylindrical body 100, this step acting as a limit stop. Simultaneously, the tongues 113 of the free release device act against the steps 117 (of which only one is visible in FIG. 10). Thus it is not possible to further rotate the knob 112 anticlockwise, whereas it can be rotated in the opposite direction, the free release device enabling the shaft 114 and hence the conveyor disc 122 to be dragged in the same direction of rotation (clockwise), until the cup 120 has been returned to the filling commencement position of FIG. 11.

As can be seen from this latter figure, tongues 121 located alternately on the two sides of the slot 128 project into the latter. The tongues 121 have a double function, namely a first function of levelling or scraping the powder in the cup 120 when this latter passes under them, and a second, deriving from the presence of the lower protuberances 123 (FIG. 10) provided at the end of the tongues 121, of inducing a vibrating effect when the protuberance 123 snaps into the cup 120 or out of it.

The combination of the two described effects enables complete emptying of the cup 120 to be obtained when as a result of the operation of the knob 112 the cup travels (outwards and back) along the slot 128 through its entire length.

In order to aid the descent of the powdered medicament through the container 124 of the inhaler 2 there is provided a second vibration-producing device consisting of a toothed sector 164 fixed to the top of the shaft 114 and hence rotatable with it, and engaged with a tongue 166 fixed to the container 124.

Consequently, when the shaft 114 rotates in one direction or the other through the predetermined angle, vibrations are automatically generated to not only aid the descent of the powdered medicament contained in the container 124 but also to aid the filling of the cup 120 in the disc conveyor 122.

As can be seen from FIG. 10, between the two holes 126 and 136 provided respectively in the intermediate disc 103 and in the plate 119, there is positioned an element having a circular sector shape when viewed in plan, and which is known hereinafter as the mobile plate 144 (shown by dashed lines in FIG. 11), rotatable about the shaft 114. The mobile plate 144 is rotated through a certain angle in the two directions by a mechanism comprising a cam 147 and cam follower 145 in the form of a prong 145 (FIG. 11) fixed to the arcuate edge of the mobile plate 144 and engaged in a cam groove 147. This latter is formed within the inner wall of an element with an arcuate surface 150 which is in contact with the inner wall of the cylindrical body 100 and is fixed at its upper end to the dispensing knob 138. Consequently, on pressing the knob 138 the arcuate element 150 moves downwards, so that the mobile plate 144 moves from a rest position shown in FIG. 11 to a dispensing position in which a hole 155 provided in the mobile plate 144 coincides with said holes 126 and 136. The hole 155 has the same dimensions as the holes 126 and 136. However, as stated, the knob 138 also simultaneously operates the plunger 106. The latter therefore completely enters the cup 120 when the knob 138 is completely pressed. Because of the coicidence between the cup 120 and the underlying holes 126, 155 and 136 of the intermediate disc 103, the mobile plate 144 and the plate 119 respectively, the dose of medicament in powder form contained in the cup 120 falls into an underlying channel 152 and collects on its base 154. The channel 152 is fixed to the cylindrical body 100 in a manner not shown in the figures. The channel 152 has an outlet aperture 158 facing a window 160 provided in the cylindrical body 100.

There is fixed to the knob 112 a mouthpiece 180, the coaxial channel 172 of which coincides with said window 160 when the knob 112 is in the dispensing position. In FIG. 10, the channel 172 of the mouthpiece 180 is shown closed by a snap-fitted removable cap 174.

In the channel 172 there is provided a device for disintegrating any particle agglomerates in the medicament to be inhaled. This device is of fixed type and consists of a helically extending channel portion 176. Specifically, the disintegration device consists (see FIG. 10) of a central shaft 186 carrying a coaxial helical element 188 occupying the entire remaining part of the channel 172 of the mouthpiece 180.

It is however apparent that other disintegration means such as a rotatable impeller can be used.

To complete the description of the inhaler 2, it is sufficient to state that if the patient places his lips about the mouthpiece 180 and sucks through the channel 172, external air is drawn through one or more apertures 178 provided in the cylindrical body 100. The apertures 178 communicate with the outside via the annular slot 184 between the knob 112 and the cylindrical body 100. The air which enters through the apertures 178 passes partly into the channel 152 via its upper mouth 182 and leaves through its exit opening 158. Because of the particular form of the channel 152 vortices are generated in the traversing air stream, to result in complete removal of the dose of medicament in powder form which has fallen onto the base 154, and which mixes with the air. The air stream loaded with powdered medicament passes through the port 160, through which there also passes the remainder of the air which had entered via the apertures 178. Thus satisfactory dispersal of the powdered medicament is obtained.

The air stream loaded with the powdered medicament then passes into the channel 172 of the mouthpiece 180, to encounter said portion of helical extension 176 which disintegrates any medicament particle agglomerates present.

Thus an air stream loaded with medicament in powder form adequately mixed with air and free of agglomerations enters the bronchial passages of the patient.

If it is required to inhale the medicament through a nostril rather than through the bronchial passages it is necessary only to fit the inhaler 2 with a suitable nasal adaptor, which can for example be snap-fitted to the described mouthpiece or can replace this latter.

The inhaler 2 also comprises a conventional dose counting device or an indicator device which warns when only a certain number of doses are left before total depletion of the medicament, so that the patient is able in good time to acquire another loaded inhaler or to recharge the inhaler if this is possible. In the illustrated case, for this purpose there is fixed on the shaft 114 a pinion 190 engaging a conventional mechanism 192 for counting doses or for warning of near depletion of the stock of medicament. The number of doses still available or the relative signal is visible through a transparent window 194 provided in the cylindrical body 100.

Instead of using a disc conveyor like the disc in the embodiment shown in FIGS. 7-11, in the inhaler according to the present invention one can obviously use a reciprocating slide conveyor which is provided with a cup shaped as a hole which is similar to the one (120) in the embodiment of FIGS. 7-11. This will entail obvious changes in the other portions and mechanisms that make up the inhaler with reciprocating slide conveyor.

I claim:

1. A multi-dose inhaler for use with medicaments in powder form, comprising:

a container means for containing the medicament;

dose measurement means for removing the medicament from said container means, said dose measurement means including a conveyor means;

said conveyor means having at least one cup of predetermined size, said cup further having two axially-oriented holes of identical size;

a mouthpiece;

a mixing chamber in fluid communication with said mouthpiece;

a plunger means for entering into and emptying said cups, said plunger means being normally disposed above said mixing chamber;

said plunger means having a reciprocable projection being of substantially the same diameter as said axially-oriented holes of said cup.

2. The multi-dose inhaler as claimed in claim 1 comprising a wall separating said dose measurement means from said mixing chamber, said wall having an aperture therein and means for opening and closing said aperture to enable a dose of medicament in powder form to fall into said mixing chamber following operation of said plunger means when said conveyor means is moved to position said axially oriented holes above said aperture.

3. The multi-dose inhaler as claimed in claim 1, including means for producing vibrations within said container means.

4. The multi-dose inhaler as claimed in claim 3, wherein said vibration-producing means is operated by the movement of said conveyor means.

5. The multi-dose inhaler as claimed in claim 1 comprising means for manually operating said conveyor means.

6. The multi-dose inhaler as claimed in claim 5, wherein said means for manually operating said conveyor means comprises a knob operatively coupled to said conveyor means to move said at least one cup between said container means and said mixing chamber.

7. The multi-dose inhaler as claimed in claim 1 comprising means for permitting manual operation of said plunger means.

8. The multi-dose inhaler as claimed in claim 7, wherein said means for manually operating said plunger means comprises a knob, to be pressed by a user's fingers, which is fixed to said plunger means, and including a return spring which returns said plunger means to its rest position when a user's fingers are released from the knob.

9. A multi-dose inhaler as claimed in claim 1 comprising means for indicating depletion of the medicament in said container means.

10. The multi-dose inhaler as claimed in claim 1, wherein said container means is rechargeable with medicament in powder form.

11. The multi-dose inhaler as claimed in claim 10, wherein said container means is removable, and said recharging is done by replacing said container means.

12. The multi-dose inhaler as claimed in claim 1, wherein the dose of medicament in powder form is to be administered nasally, and said inhaler further comprises an adapter shaped to adapt to a nostril of a patient.

13. The multi-dose inhaler as claimed in claim 1 comprising means in said mixing unit to disintegrate any medicament particle agglomerates.

* * * * *